(12) United States Patent
Shibuya et al.

(10) Patent No.: US 8,066,977 B2
(45) Date of Patent: Nov. 29, 2011

(54) AGENT FOR PERMANENT HAIR WAVING CONTAINING HETEROCYCLIC MERCAPTO COMPOUND

(75) Inventors: Akira Shibuya, Kawasaki (JP); Shinichi Yorozuya, Kawasaki (JP); Makoto Saito, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 1140 days.

(21) Appl. No.: 11/884,413

(22) PCT Filed: May 25, 2006

(86) PCT No.: PCT/JP2006/310951
§ 371 (c)(1),
(2), (4) Date: Aug. 15, 2007

(87) PCT Pub. No.: WO2006/126729
PCT Pub. Date: Nov. 30, 2006

(65) Prior Publication Data
US 2009/0208439 A1     Aug. 20, 2009

(30) Foreign Application Priority Data
May 27, 2005   (JP) .................................. 2005-155734

(51) Int. Cl.
*A61Q 5/04* (2006.01)
(52) U.S. Cl. ..................................................... 424/70.2
(58) Field of Classification Search ........................ None
See application file for complete search history.

(56) References Cited

U.S. PATENT DOCUMENTS 3,879,534 A * 4/1975 Rambacher et al. .......... 514/389

FOREIGN PATENT DOCUMENTS

| | | |
|---|---|---|
| DE | 26 14 723 A1 | 10/1977 |
| DE | 102 06 292 A1 | 8/2003 |
| EP | 1 500 386 A | 1/2005 |
| GB | 1 279 144 A | 6/1972 |
| JP | 3-271214 A | 12/1991 |
| JP | 8-291031 A | 11/1996 |
| JP | 2000-507272 A | 6/2000 |
| JP | 2003-528901 A | 9/2003 |
| WO | WO 97/03057 A | 1/1997 |
| WO | WO 2006/068276 A1 | 6/2006 |

OTHER PUBLICATIONS

Patent Abstracts of Japan, vol. 017, No. 442 (C-1097), Aug. 16, 1993 for JP-A-5-97800 (Kao Corp.), Apr. 20, 1993.

* cited by examiner

*Primary Examiner* — Jyothsna Venkat
(74) *Attorney, Agent, or Firm* — Sughrue Mion, PLLC

(57) ABSTRACT

Disclosed is an agent for permanent hair waving that can realize permanent hair waving even in the neutral to weakly acidic pH range in which irritation particularly to the skin is not significant. The agent for permanent hair waving includes at least one heterocyclic mercapto compound represented by formula (1):

$$\text{(1)}$$

wherein $R^1$ and $R^2$ each independently represent a hydrogen atom or an optionally substituted alkyl group having 1 to 5 carbon atoms; X represents —O—, —S—, —NH—, or —$NR^3$—; $R^3$ represents an alkyl group having 1 to 5 carbon atoms; n is an integer of 0 to 2; and, when n is 2, group SH may be attached to any carbon atom of an alkylene group having 2 carbon atoms.

9 Claims, No Drawings

AGENT FOR PERMANENT HAIR WAVING CONTAINING HETEROCYCLIC MERCAPTO COMPOUND

FIELD OF THE INVENTION

The present invention relates to an agent for permanent hair waving containing a heterocyclic mercapto compound and a method for permanent hair waving using the same.

BACKGROUND OF THE INVENTION

Compounds generally known also as keratin reducing substances, for example, thioglycollic acid, cysteine, acetylcysteine, and salts thereof, have hitherto been used for permanent waving for hair (hereinafter often referred to as "permanent hair waving"). Since these conventional compounds known also as keratin reducing substances have properties satisfactory for practical use under alkaline conditions in permanent hair waving, most permanent wave solutions are adjusted to an alkaline pH value of about 9.5. The permanent wave solution adjusted to the alkaline pH value, however, is known to cause damage to the hair and scalp. In order to overcome this drawback, keratin reducing substances usable in the neutral to weakly acidic pH range (pH: 3 to 7.5, 25° C.) are under development.

For example, monoglycerol esters of thioglycollic acid are disclosed as a thioglycollic acid ester having a hydroxyl group in its alcohol moiety (patent document 1). Thioglycollic acid monoglycerol esters, however, have not been put to practical use, because, for the thioglycollic acid monoglycerol esters, there is a report about sensitization that is considered to be derived from the hydroxyl group in the structure.

Further, the use of mercaptoglycollic acid amide derivatives (patent document 2) and mercaptolactic acid amide derivatives (patent document 3) for solving the skin disorder problem caused by thioglycollic acid esters is disclosed. However, it is known that mercaptocarboxylic acid amides are irritant to the skin. Mercaptocarboxylic acid amide derivatives also have a fear of causing the same sensitization. Further, disadvantageously, there is a fear of causing sensitization, irritation to the skin and the like due to unsatisfactory purification and the starting amine liberated from during storage.

Further, cysteamines claimed to exhibit the effect under weakly acidic condition have been studied (patent document 4). Cysteamines, however, suffer from many problems, for example, unsatisfactory waving properties in a weakly acidic to acidic region and the occurrence of peculiar odor from the hair after permanent waving treatment.

[Patent document 1] Japanese Patent Laid-Open No. 291031/1996
[Patent document 2] Japanese Translations of PCT Publication No. 507272/2000
[Patent document 3] Japanese Translations of PCT Publication No. 528901/2003
[Patent document 4] Japanese Patent Laid-Open No. 271214/1991

DISCLOSURE OF THE INVENTION

An object of the present invention is to provide an agent for permanent hair waving that can realize permanent hair waving even in the neutral to weakly acidic pH range in which irritation particularly to the skin is not significant.

Another object of the present invention is to provide a method for permanent hair waving using the above agent for permanent hair waving.

Under the above circumstances, the present inventors have made extensive and intensive studies and, as a result, have found that an agent for permanent hair waving, possessing a high level of waving properties, wave straightening and curly hair correcting properties and the like even in the neutral to weakly acidic pH range, can be provided by incorporating a specific heterocyclic mercapto compound as a keratin reducing substance. This has led to the completion of the present invention.

The present invention will be summarized below [1] to [10].

[1] An agent for permanent hair waving comprising at least one heterocyclic mercapto compound represented by formula (1):

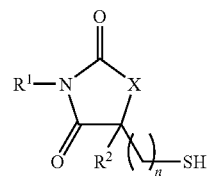

(1)

wherein $R^1$ and $R^2$ each independently represent a hydrogen atom or an optionally substituted alkyl group having 1 to 5 carbon atoms; X represents —O—, —S—, —NH—, or —$NR^3$—; $R^3$ represents an alkyl group having 1 to 5 carbon atoms; n is an integer of 0 to 2; and, when n is 2, group SH may be attached to any carbon atom of an alkylene group having 2 carbon atoms.

[2] The agent for permanent hair waving according to the above item [1], wherein $R^1$ and $R^2$ in formula (1) each independently represent a hydrogen atom, an alkyl group having 1 to 5 carbon atoms, or a substituted alkyl group having 2 to 5 carbon atoms in which two or more methylene groups are bonded through an ether bond, a thioether bond, or an amine bond.

[3] The agent for permanent hair waving according to the above item [1], wherein $R^1$ and $R^2$ in formula (1) each independently represent a hydrogen atom or an alkyl group having 1 to 4 carbon atoms.

[4] The agent for permanent hair waving according to any one of the above items [1] to [3], wherein X in formula (1) represents —NH— or —$NR^3$—.

[5] The agent for permanent hair waving according to the above item [1], wherein X in formula (1) represents —NH—, and $R^1$ and $R^2$ each independently represent a hydrogen atom or a methyl group.

[6] The agent for permanent hair waving according to the above item [1], wherein X in formula (1) represents —$NR^3$—, and $R^1$ and $R^2$ each independently represent a hydrogen atom or a methyl group.

[7] The agent for permanent hair waving according to any one of the above items [1] to [6], wherein the content of the compound represented by the formula (1) is 0.2 to 15% by mass.

[8] The agent for permanent hair waving according to any one of the above items [1] to [7], wherein the pH value is 2.5 to 8.5.

[9] The agent for permanent hair waving according to any one of the above items [1] to [8], wherein a perfume is further contained.

[10] A method for permanent hair waving comprising using the agent for permanent hair waving according to any one of the above items [1] to [9].

The agent for permanent hair waving according to the present invention has excellent practical permanent hair waving properties even in the neutral to weakly acidic pH range and, at the same time, has excellent practical waving properties even in a low concentration and, thus, is very useful for permanent hair waving. Further, the odor of the hair after the permanent waving treatment could have also been significantly improved over the conventional cysteamine agent for permanent hair waving.

BEST MODE FOR CARRYING OUT THE INVENTION

The present invention will be described in more detail.
<Heterocyclic Mercapto Compound>
Heterocyclic mercapto compounds usable in the present invention are compounds represented by formula (1)

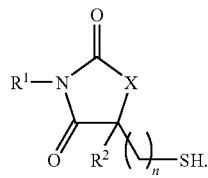

(1)

In formula (1), $R^1$ and $R^2$ each independently represent a hydrogen atom or an optionally substituted alkyl group having 1 to 5 carbon atoms; X represents —O—, —S—, —NH—, or —NR$^3$—; $R^3$ represents an alkyl group having 1 to 5 carbon atoms; n is an integer of 0 to 2; and, when n is 2, group SH may be attached to any carbon atom of an alkylene group having 2 carbon atoms.

Specifically, preferably, $R^1$ and $R^2$ each independently represent a hydrogen atom, an alkyl group having 1 to 5 carbon atoms, or a substituted alkyl group having 2 to 5 carbon atoms in which two or more methylene groups are bonded through an ether bond, a thioether bond, or an amine bond.

More specifically, $R^1$ and $R^2$, which may be the same or different, preferably represent a hydrogen atom or an alkyl group having 1 to 5 carbon atoms such as a methyl, ethyl, n-propyl, isopropyl, n-butyl, isobutyl, tert-butyl, n-pentyl, or isopentyl group from the viewpoint of production on a commercial scale. From the viewpoint of improving the water solubility, $R^1$ and $R^2$, which may be the same or different, may represent a substituted alkyl group of which the total number of carbon atoms is 2 to 5 such as a 2-methoxyethyl, 2-ethoxyethyl, 2-propoxyethyl, 2-methylaminoethyl, 2-ethylaminoethyl, 2-methylthioethyl, 2-ethylthioethyl, or 2-propylthioethyl group.

More preferably, $R^1$ and $R^2$ each independently represent a hydrogen atom or an alkyl group having 1 to 4 carbon atoms, still more preferably each independently represent a hydrogen atom or a methyl group.

X generally represents —O—, —S—, —NH—, or —NR$^3$—. Preferably, $R^3$ represents an alkyl group having 1 to 5 carbon atoms. From the viewpoint of production on a commercial scale, more preferably, $R^3$ represents an alkyl group having 1 to 4 carbon atoms such as a methyl, ethyl, n-propyl, isopropyl, n-butyl, isobutyl, or tert-butyl group. Among them, a methyl or ethyl group is still more preferred.

Specifically, when X represents —O—, —S—, —NH—, —N(CH$_3$)—, or —N(CH$_2$CH$_3$)—, the solubility of the compound in a permanent wave solution which is in many cases used as an aqueous solution is relatively high. This is advantageous from the viewpoint of liquid preparation. More preferred are —NH—, —N(CH$_3$)—, and —N(CH$_2$CH$_3$)—.

When n is an integer of 0 to 2 and, in this case, is 2, group SH may be attached to any carbon atom of an alkylene group having 2 carbon atoms. From the viewpoint of easy production on a commercial scale, however, n is preferably 0 (zero) (that is, group SH is attached directly to a carbon atom at the 5-position constituting the heterocyclic ring) or 1.

Examples of such heterocyclic mercapto compounds include compounds having an imidazolidine, oxazolidine, or thiazolidine ring as a basic skeleton.

Specific examples of compounds having an imidazolidine ring as a basic skeleton include 5-mercaptohydantoin, 1-methyl-5-mercaptohydantoin, 1-ethyl-5-mercaptohydantoin, 1-propyl-5-mercaptohydantoin, 1-isopropyl-5-mercaptohydantoin, 1-n-butyl-5-mercaptohydantoin, 1-isobutyl-5-mercaptohydantoin, 1-tert-butyl-5-mercaptohydantoin, 3-methyl-5-mercaptohydantoin, 3-ethyl-5-mercaptohydantoin, 3-propyl-5-mercaptohydantoin, 3-isopropyl-5-mercaptohydantoin, 3-n-butyl-5-mercaptohydantoin, 3-isobutyl-5-mercaptohydantoin, 3-tert-butyl-5-mercaptohydantoin, 1-methyl-3-methyl-5-mercaptohydantoin, 1-ethyl-3-methyl-5-mercaptohydantoin, 1-propyl-3-methyl-5-mercaptohydantoin, 1-isopropyl-3-methyl-5-mercaptohydantoin, 1-n-butyl-3-methyl-5-mercaptohydantoin, 1-isobutyl-3-methyl-5-mercaptohydantoin, 1-tert-butyl-3-methyl-5-mercaptohydantoin, 1-methyl-3-ethyl-5-mercaptohydantoin, 1-ethyl-3-ethyl-5-mercaptohydantoin, 1-propyl-3-ethyl-5-mercaptohydantoin, 1-isopropyl-3-ethyl-5-mercaptohydantoin, 1-n-butyl-3-ethyl-5-mercaptohydantoin, 1-isobutyl-3-ethyl-5-mercaptohydantoin, 1-tert-butyl-3-ethyl-5-mercaptohydantoin, 1-methyl-3-propyl-5-mercaptohydantoin, 1-ethyl-3-propyl-5-mercaptohydantoin, 1-propyl-3-propyl-5-mercaptohydantoin, 1-isopropyl-3-propyl-5-mercaptohydantoin, 1-n-butyl-3-propyl-5-mercaptohydantoin, 1-isobutyl-3-propyl-5-mercaptohydantoin, 1-tert-butyl-3-propyl-5-mercaptohydantoin, 5-mercapto-5-methylhydantoin, 1-methyl-5-mercapto-5-methylhydantoin, 1-ethyl-5-mercapto-5-methylhydantoin, 1-propyl-5-mercapto-5-methylhydantoin, 1-isopropyl-5-mercapto-5-methylhydantoin, 1-n-butyl-5-mercapto-5-methylhydantoin, 1-isobutyl-5-mercapto-5-methylhydantoin, 1-tert-butyl-5-mercapto-5-methylhydantoin, 3-methyl-5-mercapto-5-methylhydantoin, 3-ethyl-5-mercapto-5-methylhydantoin, 3-propyl-5-mercapto-5-methylhydantoin, 3-isopropyl-5-mercapto-5-methylhydantoin, 3-n-butyl-5-mercapto-5-methylhydantoin, 3-isobutyl-5-mercapto-5-methylhydantoin, 3-tert-butyl-5-mercapto-5-methylhydantoin, 1-methyl-3-methyl-5-mercapto-5-methylhydantoin, 1-ethyl-3-methyl-5-mercapto-5-methylhydantoin, 1-propyl-3-methyl-5-mercapto-5-methylhydantoin, 1-isopropyl-3-methyl-5-mercapto-5-methylhydantoin, 1-n-butyl-3-methyl-5-mercapto-5-methylhydantoin, 1-isobutyl-3-methyl-5-mercapto-5-methylhydantoin, 1-tert-butyl-3-methyl-5-mercapto-5-methylhydantoin, 1-methyl-3-ethyl-5-mercapto-5-methylhydantoin, 1-ethyl-3-ethyl-5-mercapto-5-methylhydantoin, 1-propyl-3-ethyl-5-mercapto-5-methylhydantoin, 1-isopropyl-3-ethyl-5-mercapto-5-methylhydantoin, 1-n-butyl-3-ethyl-5-mercapto-5-methylhydantoin, 1-isobutyl-3-ethyl-5- mercapto-5-methylhydantoin, 1-tert-butyl-3-ethyl-5-mercapto-5-methylhydantoin, 1-methyl-3-propyl-5-mercapto-5-methylhydantoin, 1-ethyl-3-propyl-5-mercapto-5-methylhydantoin, 1-propyl-3-propyl-5-mercapto-5-methylhydantoin, 1-isopropyl-3-propyl-5-mercapto-5-methylhydantoin, 1-n-butyl-3-propyl-5-mercapto-5-methylhydantoin, 1-isobutyl-3-propyl-5-mercapto-5-methylhydantoin, 1-tert-butyl-3-propyl-5-mercapto-5-methylhydantoin, 5-mercaptomethylhydantoin, 1-methyl-5-mercaptomethylhydantoin, 1-ethyl-5-mercaptomethylhydantoin, 1-propyl-5-mercaptomethylhydantoin,
1-isopropyl-5-mercaptomethylhydantoin, 1-n-butyl-5-mercaptomethylhydantoin, 1-isobutyl-5-mercaptomethylhydantoin, 1-tert-butyl-5-mercaptomethylhydantoin, 3-methyl-5-mercaptomethylhydantoin, 3-ethyl-5-mercaptomethylhydantoin, 3-propyl-5-mercaptomethylhydantoin, 3-isopropyl-5-mercaptomethylhydantoin, 3-n-butyl-5-mercaptomethylhydantoin, 3-isobutyl-5-mercaptomethylhydantoin, 3-tert-butyl-5-mercaptomethylhydantoin, 1-methyl-3-methyl-5-mercaptomethylhydantoin, 1-ethyl-3-methyl-5-mercaptomethylhydantoin, 1-propyl-3-methyl-5-mercaptomethylhydantoin, 1-isopropyl-3-methyl-5-mercaptomethylhydantoin, 1-n-butyl-3-methyl-5-mercaptomethylhydantoin, 1-isobutyl-3-methyl-5-mercaptomethylhydantoin,
1-tert-butyl-3-methyl-5-mercaptomethylhydantoin, 1-methyl-3-ethyl-5-mercaptomethylhydantoin, 1-ethyl-3-ethyl-5-mercaptomethylhydantoin, 1-propyl-3-ethyl-5-mercaptomethylhydantoin, 1-isopropyl-3-ethyl-5-mercaptomethylhydantoin, 1-n-butyl-3-ethyl-5-mercaptomethylhydantoin, 1-isobutyl-3-ethyl-5-mercaptomethylhydantoin, 1-tert-butyl-3-ethyl-5-mercaptomethylhydantoin, 1-methyl-3-propyl-5-mercaptomethylhydantoin, 1-ethyl-3-propyl-5-mercaptomethylhydantoin, 1-propyl-3-propyl-5-mercaptomethylhydantoin, 1-isopropyl-3-propyl-5-mercaptomethylhydantoin, 1-n-butyl-3-propyl-5-mercaptomethylhydantoin, 1-isobutyl-3-propyl-5-mercaptomethylhydantoin, 1-tert-butyl-3-propyl-5-mercaptomethylhydantoin, 5-mercaptomethyl-5-methylhydantoin,
1-methyl-5-mercaptomethyl-5-methylhydantoin, 1-ethyl-5-mercaptomethyl-5-methylhydantoin, 1-propyl-5-mercaptomethyl-5-methylhydantoin, 1-isopropyl-5-mercaptomethyl-5-methylhydantoin, 1-n-butyl-5-mercaptomethyl-5-methylhydantoin, 1-isobutyl-5-mercaptomethyl-5-methylhydantoin, 1-tert-butyl-5-mercaptomethyl-5-methylhydantoin, 3-methyl-5-mercaptomethyl-5-methylhydantoin, 3-ethyl-5-mercaptomethyl-5-methylhydantoin,
3-propyl-5-mercaptomethyl-5-methylhydantoin, 3-isopropyl-5-mercaptomethyl-5-methylhydantoin, 3-n-butyl-5-mercaptomethyl-5-methylhydantoin, 3-isobutyl-5-mercaptomethyl-5-methylhydantoin, 3-tert-butyl-5-mercaptomethyl-5-methylhydantoin, 1-methyl-3-methyl-5-mercaptomethyl-5-methylhydantoin, 1-ethyl-3-methyl-5-mercaptomethyl-5-methylhydantoin, 1-propyl-3-methyl-5-mercaptomethyl-5-methylhydantoin, 1-isopropyl-3-methyl-5-mercaptomethyl-5-methylhydantoin, 1-n-butyl-3-methyl-5-mercaptomethyl-5-methylhydantoin, 1-isobutyl-3-methyl-5-mercaptomethyl-5-methylhydantoin, 1-tert-butyl-3-methyl-5-mercaptomethyl-5-methylhydantoin, 1-methyl-3-ethyl-5-mercaptomethyl-5-methylhydantoin,
1-ethyl-3-ethyl-5-mercaptomethyl-5-methylhydantoin, 1-propyl-3-ethyl-5-mercaptomethyl-5-methylhydantoin, 1-isopropyl-3-ethyl-5-mercaptomethyl-5-methylhydantoin, 1-n-butyl-3-ethyl-5-mercaptomethyl-5-methylhydantoin, 1-isobutyl-3-ethyl-5-mercaptomethyl-5-methylhydantoin, 1-tert-butyl-3-ethyl-5-mercaptomethyl-5-methylhydantoin, 1-methyl-3-propyl-5-mercaptomethyl-5-methylhydantoin, 1-ethyl-3-propyl-5-mercaptomethyl-5-methylhydantoin, 1-propyl-3-propyl-5-mercaptomethyl-5-methylhydantoin, 1-isopropyl-3-propyl-5-mercaptomethyl-5-methylhydantoin, 1-n-butyl-3-propyl-5-mercaptomethyl-5-methylhydantoin, 1-isobutyl-3-propyl-5-mercaptomethyl-5-methylhydantoin, and 1-tert-butyl-3-propyl-5-mercaptomethyl-5-methylhydantoin.

Specific examples of compounds having an oxazolidine ring as a basic skeleton include 5-mercaptoxazolidine-2,4-dione, 5-mercapto-3-methyloxazolidine-2,4-dione, 5-mercapto-3-ethyloxazolidine-2,4-dione, 5-mercapto-5-methyloxazolidine-2,4-dione, 5-mercapto-3,5-dimethyloxazolidine-2,4-dione, 5-mercaptomethyl-oxazolidine-2,4-dione, and 5-mercaptomethyl-3,5-dimethyloxazolidine-2,4-dione.

Specific examples of compounds having a thiazolidine ring as a basic skeleton include 5-mercaptothiazolidine-2,4-dione, 5-mercapto-3-methylthiazolidine-2,4-dione, 5-mercapto-3-ethylthiazolidine-2,4-dione, 5-mercapto-5-methylthiazolidine-2,4-dione, 5-mercapto-3,5-dimethylthiazolidine-2,4-dione, 5-mercaptomethyl-thiazolidine-2,4-dione, and 5-mercaptomethyl-3,5-dimethylthiazolidine-2,4-dione.

Among them, 5-mercaptohydantoin, 1-methyl-5-mercaptohydantoin, 1-ethyl-5-mercaptohydantoin, 3-methyl-5-mercaptohydantoin, 3-ethyl-5-mercaptohydantoin, 1-methyl-3-methyl-5-mercaptohydantoin, 1-ethyl-3-methyl-5-mercaptohydantoin, 1-methyl-3-ethyl-5-mercaptohydantoin, 1-ethyl-3-ethyl-5-mercaptohydantoin, 5-mercapto-5-methylhydantoin, 1-methyl-5-mercapto-5-methylhydantoin, 5-mercaptomethylhydantoin, 1-methyl-5-mercaptomethylhydantoin, 3-methyl-5-mercaptomethylhydantoin, and 1-methyl-3-methyl-5-mercaptomethylhydantoin;

5-mercaptoxazolidine-2,4-dione and 5-mercapto-3-methyloxazolidine-2,4-dione; and 5-mercaptothiazolidine-2,4-dione, 5-mercapto-3-methylthiazolidine-2,4-dione, 5-mercapto-3-ethylthiazolidine-2,4-dione, 5-mercapto-5-methylthiazolidine-2,4-dione, 5-mercapto-3,5-dimethylthiazolidine-2,4-dione, 5-mercaptomethyl-thiazolidine-2,4-dione, and 5-mercaptomethyl-3,5-dimethylthiazolidine-2,4-dione are preferred from the viewpoints of permanent waving properties and production on a commercial scale.

These compounds can be produced by a conventional method.

For example, among the above heterocyclic mercapto compounds, compounds in which the mercapto group is attached directly to a carbon atom at the 5-position constituting the heterocyclic ring (in formula (1), n is 0 (zero)) are produced by reacting a commercially available hydantoin compound, oxazolidine compound, or thiazolidine compound with a halogen such as bromine in a solvent such as dioxane to synthesize a halide (for details, see Japanese Patent Laid-Open No. 278116/1995) and blowing a hydrogen sulfide gas into the halide at a low temperature.

On the other hand, mercapto compounds in which a mercapto group is attached to a carbon atom at the 5-position constituting the heterocyclic ring through a methylene or ethylene group, or mercapto compounds in which a mercapto group and a methyl group are attached to a carbon atom at the 5-position constituting the heterocyclic ring through a methine group (in formula (1), n is 1 or 2), may be synthesized by reacting a commercially available halogenated aldehyde compound or halogenated ketone compound with sodium cyanate to synthesize a halide (for details, see Japanese Patent Laid-Open No. 043309/2004) and reacting the halide thus obtained with sodium sulfide or sodium hydrosulfide in a polar solvent.

The incorporation of the heterocyclic mercapto compound in the agent for permanent hair waving is advantageous in that action at a pH value low enough to avoid the influence on the hair is possible, and, at the same time, even in a low concentration, a high level of waving efficiency and wave straightening, curly hair correcting or other properties can be realized, and the influence on the skin is also small. The reason for this has not been elucidated yet, but is believed to be as follows. The heterocyclic mercapto compound contains a heterocyclic ring and thus is likely to be oxidized and thus can exhibit a function which is satisfactory from the viewpoint of practical performance even in the weakly acid to neutral pH range in which the conventional mercapt compounds could not have been practically used.

<Agent for Permanent Hair Waving>

The agent for permanent hair waving includes at least one of the above heterocyclic mercapto compounds. That is, one of or a combination of at least two of the above heterocyclic mercapto compounds may be used.

Specifically, the content of the heterocyclic mercapto compound in the agent for permanent hair waving represented by formula (1) is generally 0.2 to 15% by mass, more preferably 1 to 10% by mass. When the content of the heterocyclic mercapto compound falls within the above-defined range, damage to the hair and skin is not significant and a high waving efficiency can be maintained. When the content of the heterocyclic mercapto compound is less than 0.2% by mass, in some cases, the properties as the agent for permanent hair waving cannot be substantially provided. On the other hand, when the content of the heterocyclic mercapto compound exceeds 15% by mass, in some cases, excessive curling of the hair and the acceleration of partial peeling of cuticles, which lead to severe damage to the hair, disadvantageously take place.

In the agent for permanent hair waving according to the present invention, the heterocyclic mercapto compound represented by formula (1) may be used solely as the keratin reducing substance. Alternatively, the heterocyclic mercapto compound represented by formula (1) may be used in combination with, for example, thioglycollic acid, thiolactic acid, cysteine, acetylcysteine, cysteamines, acylcysteamines, and their salts and sulfites, which have been used conventionally as the keratin reducing substance in such an amount that does not sacrifice the effect of the present invention.

In addition to the above heterocyclic mercapto compounds, conventional perfumes may be further incorporated in the agent for permanent hair waving according to the present invention to mask the odor of the heterocyclic mercapto compound according to the present invention for a further improvement.

The perfume may be at least one member selected from the group consisting of (A) hydrocarbons, (B) alcohols, (C) phenols, (D) aldehydes and/or acetals, (E) ketones and/or ketals, (F) ethers, (G) synthetic musks, (H) acids, (I) lactones, (J) esters, (K) nitrogen- and/or sulfur- and/or halogen-containing compounds, and (L) natural perfumes.

Specific examples thereof are disclosed in Japanese Patent Laid-Open No. 137758/2003.

Hydrocarbons (A) are not particularly limited so long as they are volatile organic compounds constituted by carbon and hydrogen, and examples thereof include aliphatic hydrocarbons, alicyclic hydrocarbons, terpene hydrocarbons, and aromatic hydrocarbons. More specific examples thereof include 1,3,5-undecatriene, p-cymene, α-pinene, 2,6,6-trimethyl-1-crotonylcyclohexane, 7-methyl-3-methylene-1,6-octadiene, p-ethylstyrene, α-p-dimethylstyrene, styrene, decalin, decane, tetradecane, tetralin, dodecane, tridecane, tridecene, naphthalene, nonane, nonene, norbornane, norbornene, hexadecane, hexane, heptadecadiene, heptadecane, heptadecene, heptane, and pentadecane.

Alcohols (B) are not particularly limited so long as they are volatile hydroxyl-containing organic compounds, and examples thereof include aliphatic alcohols, alicyclic alcohols, terpene alcohols, and aromatic alcohols. More specific examples thereof include 10-undecenol, α-phenykyl alcohol, isoborneol, dihydromyrcenol, nerol, nerolidol, bacdanol (2-ethyl-4-(2,2,3-trimethyl-3-cyclopenten-1-yl)-2-buten-1-ol), 2-methyl-4-(2,2,3-trimethyl-3-cyclopentenyl)-2-butenol, 2-methyl-4-(2,2,3-trimethyl-3-cyclopenten-1-yl)-2-buten-1-ol, 3-methyl-5-(2,2,3-trimethyl-3-cyclopenten-1-yl)-pentan-2-ol, 3-methyl-5-phenylpentanol, β,γ-hexenol, trans-2-hexenol, cis-p-menthan-7-ol, and p-methoxyphenethyl alcohol.

Phenols (C) are not particularly limited so long as they are phenolic compounds and derivatives thereof that are organic compounds which give out perfume. Examples thereof include monohydric, dihydric and trihydric phenol compounds, polyphenols, or ether derivatives of these compounds. Specific examples thereof include p-cresol, isoeugenol, estragole, eugenol, hinokitiol, methoxybenzene, resorcinol dimethyl ether, and shogaol.

Aldehydes and/or acetals (D) are not particularly limited so long as they are volatile organic compounds having an aldehyde group and/or an acetal group in the molecule thereof. Examples thereof include aliphatic aldehydes and acetals, terpene aldehydes and acetals, aromatic aldehydes and acetals. More specific examples thereof include 10-undecenal, 2,4-dimethyl-4,4a,5,9b-tetrahydroindeno[1,2d]-1,3-dioxine, 2,4-decadienal, 2,6-nonadienal, 2-butyl-4,4,6-trimethyl-1,3-dioxane, 2-hexyl-5-methyl-1,3-dioxolane, 2-methylundecanal, 2-methylundecanal dimethyl acetals, methyldecanal, methylnonyl acetaldehyde dimethyl acetals, methyl vanillin, methoxy dicyclopentadiene carboxyaldehyde, and methoxycitronellal.

Ketones and/or ketals (E) are not particularly limited so long as they are volatile organic compounds having a ketone group and/or a ketal group in the molecule thereof. Examples thereof include aliphatic ketone and ketals, terpene ketones and ketals, aromatic ketones and ketals. Specific examples thereof include 2-sec-butylcyclohexanone, cis-jasmone, dihydrocarvone, dihydrojasmone, methylionone, methylcyclopentenolone, methylheptenone, menthone, raspberry ketone, methyl α-furyl ketone, methylisopropyl ketone, methyl iritone, methyl cedrilone, methyltetrahydrofuranone, and 4-(1-ethoxyvinyl)-3,3,5,5-tetramethylcyclohexanone.

Ethers (F) are not particularly limited so long as they are volatile organic compounds having an ether group in the molecule thereof. Examples thereof include aliphatic ethers, terpene ethers, and aromatic ethers. Specific examples thereof include 1,4-cineol, 1,8-cineol, nerol oxide, phenyl ethyl methyl ether, madrox, linalool oxide, 13-oxabicyclo[10.3.0]pentadecane, n-decyl vinyl ether, tert-butyl hydroquinone dimethyl ether, dimethyl ether, tetrahydrofuran, propylene glycol diethyl ether, and propylene glycol dimethyl ether.

Synthetic musks (G) are not particularly limited so long as they are organic compounds having musk fragrance or musk-like fragrance. Examples thereof include 10-oxahexadecanolide, 11-oxahexadecanolide, 12-oxahexadecanolide, ambrettolide, ambreton, exaltolide, exaltone, galaxolide, cyclohexadecanolide, cyclopentadecanolide, cyclopentadecanone, civetone, cervolide, celestolide, tonalid, phantolide, pentalide, formylethyltetramethyltetralin, musk tibetene, muscone, moskene, musk amberette, and versalide.

Acids (H) are not particularly limited so long as they are organic compounds having a carboxyl group in the molecule thereof. Examples thereof include phenylacetic acid, 2-ethylbutyric acid, 2-ethylhexanoic acid, 2-decenoic acid, 2-hexenoic acid, 2-methyl-2-pentenoic acid, 2-methylbutyric acid, 2-methylheptanoic acid, 4-pentenoic acid, 4-methylpentanoic acid, acetic acid, isovaleric acid, isobutyric acid, benzoic acid, malic acid, maleic acid, and malonic acid.

Lactones (I) are not particularly limited so long as they are volatile organic compounds having a lactone group in the molecule thereof. Examples thereof include aliphatic lactones, terpene lactones, and aromatic lactones. Specific examples thereof include 6-methylcoumarin, α-angelicalactone, γ-n-butyrolactone, γ-undecalactone, γ-octalactone, γ-decalactone, γ-nonalactone, γ-valerolactone, γ-hexalactone, γ-heptalactone, δ-2-decenolactone, δ-undecalactone, δ-octalactone, δ-decalactone, δ-tetradecalactone, δ-dodecalactone, δ-tridecalactone, δ-nonalactone, δ-hexalactone, ε-decalactone, and ε-dodecalactone.

Esters (J) are not particularly limited so long as they are volatile organic compounds having an ester group in the molecule thereof. Examples thereof include aliphatic esters, terpene ester, and aromatic esters. Specific examples thereof include 1-ethinyl cyclohexyl acetate, aphelmate (α,3,3-trimethylcyclohexane methylformate), dimethyl succinate, dimethylphenylethylcarbynyl acetate, dimethyl phthalate, dimethylbenzylcarbynyl acetate, dimethylbenzylcarbynyl isobutyrate, dimethylbenzylcarbynyl butyrate, dimethylbenzylcarbynyl propionate, 2,2,6-trimethylcyclohexanecarboxylic acid ethyl ester, methyl dihydrojasmonate, and rosephenone.

Nitrogen- and/or sulfur- and/or halogen-containing compounds (K) are not particularly limited so long as they are fragrant organic compounds containing nitrogen, sulfur, or a halogen in the molecule thereof. Examples thereof include 2-tert-butylquinoline, 2-isobutylquinoline, geranylnitrile, citronellylnitrile, 2-naphthylmercaptan, 2-pentylpyridine, 2-methyl-3-butanethiol, 2-methyl-3-furanthiol, limonene thiol, allyl isothiocyanate, allylmercaptan, isopropylmercaptan, capsaicin, quinine, thialdine, nonanoylvanillylamide, p-dichlorobenzene, bromostyrole, benzyl isothiocyanate, benzyl cyanide, methional, methionol, and mercaptoacetic acid.

Natural perfumes (L) are not particularly limited, and examples thereof include almond oil, angelica oil, ylang ylang oil, winter green oil, elemi oil, oakmoss absolute, orange oil, chamomile oil, caraway oil, guaiac wood oil, costus oil, cypress oil, sandalwood oil, cystlabdanum oil, cedarwood oil, sweet fennel oil, spearmint oil, sage oil, thyme oil, tansy oil, tuberose absolute, tolu balsam, nutmeg oil, neroli bigarade oil, basil oil, hyssop oil, Japanese cypress oil, buchu oil, bay oil, peppermint oil, bois de rose oil, marjoram oil, mimosa absolute, musk tonquin tincture, mace oil, eucalyptus oil, lime oil, lavender oil, rue oil, lemon oil, and rosemary oil. These natural substances may also be used in various forms such as essential oils, resinoids, balsam, absolute, concrete, and tincture.

These perfumes are excellent in the capability to mask odor derived from heterocyclic mercapto compounds and the like and, at the same time, are less likely to cause a significant deterioration in fragrance and has excellent stability with time over a long period of time. These perfumes may be used alone or in a combination of two or more of them depending upon purposes and consumer's preference. The combined use of a plurality of these perfumes can offer a better masking effect.

In the present invention, these perfumes are not particularly limited so long as they are contained in such an amount that can mask odor. In general, the content of these perfumes based on the heterocyclic mercapto compound of 100 parts by mass is preferably 0.01 to 50 parts by mass.

The agent for permanent hair waving according to the present invention may contain conventional additives in such an amount that does not sacrifice the effect of the present invention, from the viewpoint of improving hair waving properties and sense of use.

Such additives include surfactants, foaming/detergent aids, superfatting agents, thickeners, viscosity modifiers, opaquers, ultraviolet absorbers, preservatives, anti-scurf agents, germicidal-preservative agents, hair protective agents, wetting agents, emulsifiers, penetration promoting agents, buffers, pH adjustors, chelating agents, dyes, stabilizers, and pearl agents. If necessary, beautification components and other components commonly used in cosmetic preparations may be incorporated.

Surfactants include:

anionic surfactants such as sodium laurylsulfate, sodium polyoxyethylene lauryl ether sulfate, coconut fatty acid methyl taurine sodium, and lauroyl methyl alanine sodium;

amphoteric surfactants such as lauryl dimethylaminoacetic acid betaine, imidazoline activating agents, and coconut fatty acid amide propyl betaine;

cationic surfactants such as cetyltrimethylammonium chloride, stearyltrimethylammonium chloride, and behenyltrimethylammonium chloride; and nonionic surfactants such as alkylalkanolamides.

Thickeners include:

polymeric compounds such as carboxymethylcellulose, carboxyvinyl polymer, hydroxyethylcellulose, hydroxypropylcellulose, xanthan gum, carageenan, alginate, pectin, tragacanth, and polyvinylpyrrolidone;

higher alcohols such as lauryl alcohol, cetyl alcohol, stearyl alcohol, isostearyl alcohol, oleyl alcohol, and behenyl alcohol;

fatty acids such as lauric acid, myristic acid, palmitic acid, stearic acid, behenic acid, oleic acid, undecylic acid, and isostearic acid; and kaolin.

Wetting agents or emulsifiers include glycerin, diglycerin, propylne glycol, dipropylene glycol, 1,3-butanediol, polyethylene glycol, sorbitol, plant extract, vitamins, hyaluronic acid salts, chondroitin sulfuric acid salts, and the above cationic surfactants, anionic surfactants, amphoteric surfactants, and nonionic surfactants, and, further, ether-type nonionic surfactants such as polyoxyethylene oleyl ether, polyoxyethylene stearyl ether, polyoxyethylene cetyl ether, polyoxyethylene octyl phenyl ether, polyoxyethylene dodecyl phenyl ether, and polyoxyethylene nonyl ether; and silicone derivatives such as dimethylpolysiloxane, methylphenylpolysiloxane, amino modified silicone oils, alcohol modified silicone oils, fluorine modified silicone oils, polyether modified silicone oil, and alkyl modified silicone oils.

Penetration promoting agents include ethanol, propanol, isopropanol, 1,2-propylene glycol, 1,3-butnediol, glycerin, ethyl carbitol, benzyl alcohol, benzyloxy ethanol, urea, and 2-methylpyrrolidone.

Buffers include inorganic buffers and, further, buffers including basic amino acids such as alginine and lysine, and organic acids such as citric acid salts.

pH adjustors include inorganic acids such as hydrochloric acid and phosphoric acid, or inorganic acid salts such as disodium hydrogenphosphate, and sodium dihydrogenphosphate;

organic acids such as citric acid, malic acid, lactic acid, succinic acid, and oxalic acid, or their sodium salts; and alkaline chemicals such as ammonia, diethanolamine, triethanolamine, sodium hydroxide, potassium hydroxide, sodium carbonate, sodium hydrogencarbonate, potassium carbonate, and potassium hydrogencarbonate.

Chelating agents include edetic acid and its metal salts.

Other additives include:

medicinal oils such as paraffin, liquid paraffin, beeswax, squalane, jojoba oil, olive oil, ester oil, triglyceride, petrolatum, and lanoline; and hair protective components, for example, hydrolyzates of collagen and keratin and their derivatives.

The agent for permanent hair waving according to the present invention may be produced by dissolution, dispersion, emulsification, suspension or the like of the heterocyclic mercapto compound represented by formula (1), either alone or optionally together with the above-described other components, in a solvent.

Preferred solvents include water, alcohols and ethers. Water is more preferred from the viewpoint of general usages. In general, the amount of the solvent is the balance obtained by subtracting the total amount of the components other than the solvent from 100% by mass.

The agent for permanent hair waving according to the present invention may be previously prepared, or alternatively may be prepared by in-use preparation, that is, by mixing a plurality of agents together immediately before use.

For example, in the case of the in-use preparation, a method may be adopted in which an agent containing components other than the heterocyclic mercapto compound represented by formula (1) is prepared and a solution, prepared by diluting the heterocyclic mercapto compound with an additive such as a swelling agent or a penetration promoting agent, is mixed and dissolved in the agent.

It is needless to say that the agent for permanent hair waving according to the present invention can be used on an alkaline side. Further, the agent for permanent hair waving according to the present invention can be used in a neutral to weakly acidic pH range which is lower than the pH range adopted in the prior art technique using the keratin reducing substances. In this pH range, a better waving effect can be attained.

Accordingly, the pH value of the agent for permanent hair waving is not particularly limited. The pH value, however, is preferably 2.5 to 9.0, more preferably 2.5 to 8.5, still more preferably 4.0 to 8.0, most preferably 4.0 to 7.5. Here the pH value is a value measured with a KCL supply-type composite electrode (PH82-21-J, manufactured by Yokogawa Electric Corp.) at a temperature of 23° C.

When the pH value of the agent for permanent hair waving is in the above-defined range, the level of skin irritation is low and, for example, damage to the hair is less likely to occur.

The agent can be adjusted to the above pH range, for example, by adding the pH adjustor to the agent.

The agent for permanent hair waving according to the present invention may be in any form so long as the agent contains the heterocyclic mercapto compound represented by formula (1). For example, the agent for permanent hair waving according to the present invention may be in a liquid, foam, gel, cream, or paste form and may be used as various types of agents such as liquid, spray, aerosol, cream, and gel types depending upon the form of the agent.

<Permanent Hair Waving Method>

The permanent hair waving method according to the present invention is not particularly limited so long as the above agent for permanent hair waving is used. Further, use of the agent for permanent hair waving also is not particularly limited.

A method comprising the following steps (1) to (4) may be mentioned as an example of the permanent hair waving method according to the present invention. The permanent hair waving refers to the whole permanent waving treatment of the hair including permanent waving for the hair, straightening of hair waving, and curly hair correction.

(1) Hair is moistened with a first liquid for permanent hair waving containing a heterocyclic mercapto compound represented by formula (1), and the hair is then convolved with a rod for shaping the hair. Alternatively, a method may also be adopted in which the hair moistened with water is wound around the rod and is then wetted with the first liquid for permanent hair waving. In correcting the curly hair, the rod is not used.

(2) After wetting with the liquid chemical, the hair is allowed to stand at room temperature. In this case, heating to a temperature of about 30 to 40° C. is preferred.

(3) The hair is wetted with an oxidizing agent-containing composition (a second liquid for permanent hair waving) to oxidize the heterocyclicmercapto compound and to fix the shape of the hair.

(4) The rod is removed from the shape-fixed hair, and the hair is washed, is shampooed, and is dried.

Commonly used aqueous solution having a sodium bromate concentration of about 3 to 8% by mass and diluted solution of hydrogen peroxide or sodium perborate commonly used in step (3) are usable as the composition containing an oxidizing agent.

The method for permanent hair waving according to the present invention is advantageous in that, by virtue of the use of the agent for permanent hair waving, the influence on the skin is low, the sensitizing property is weak, and, further, the waving efficiency of the hair is excellent.

EXAMPLES

The present invention will be further described with reference to the following Examples. However, it should be noted that the present invention is not limited to these Examples. In the following Examples, "%" and "parts" are by mass unless otherwise specified.

Synthesis Example 1

<Synthesis of 5-mercaptohydantoin>

Hydantoin (100 g (1 mol), manufactured by Junsei Chemical Corporation) was mixed with 500 mL of dioxane (manufactured by Junsei Chemical Corporation) and 160 g of bromine (1 mol; manufactured by Junsei Chemical Corporation) at room temperature, and the mixture was gradually heated to 60° C., and the mixture was stirred for 45 min. After cooling to room temperature, the solvent was removed by distillation, and the residue was dried under reduced pressure to give a crude crystal of 5-bromohydantoin.

A solution prepared by dissolving the above crude crystal of 5-bromohydantoin in 600 g of dioxane was added dropwise through a dropping funnel to 720 g of dioxane in which hydrogen sulfide gas (manufactured by Sumitomo Chemical Engineering Co., Ltd.) had been satisfactorily dissolved until saturation had occurred at 13° C., while maintaining the temperature at 13° C. with stirring. The reaction solution was held at 13° C. and was stirred for 24 hr. Subsequently, the powder precipitated in the reaction solution was collected and removed by Kiriyama type funnel (suction funnel). The filtrate was concentrated under reduced pressure to give 165 g of oily matter. Purified water (800 g, water prepared by distillation and then ion exchange treatment) was added to the oily matter, and the mixture was heated to 40° C. for dissolution. The solution was slowly cooled to 5° C. in an ice bath for crystallization. The precipitated crystal was collected through Kiriyama type funnel to give 5-mercaptohydantoin as a white crystal (23 g (0.17 mol), yield 17% as calculated based on the starting compound hydantoin).

Synthesis Example 2

<Synthesis of 5-mercapto-1-methylhydantoin>

1-Methylhydantoin (114 g (1 mol); manufactured by Junsei Chemical Corporation) was dissolved in 1000 mL of dioxane (manufactured by Junsei Chemical Corporation). Trifluoroboron ether complex (0.1 g; manufactured by Tokyo Chemical Industry Co., Ltd.) was added to the solution, and the temperature was raised to 70° C. with stirring. Bromine (160 g (1 mol); manufactured by Junsei Chemical Corporation) was added dropwise thereto at 70° C. over a period of about 60 min. After the completion of dropwise addition, the solvent was removed by distillation under reduced pressure to give a crude crystal of 5-bromo-1-methylhydantoin.

A solution prepared by dissolving the above crude crystal of 5-bromo-1-methylhydantoin in 350 g of dioxane was added dropwise through a dropping funnel to 1000 g of dioxane in which hydrogen sulfide gas (manufactured by Sumitomo Chemical Engineering Co., Ltd.) had been satisfactorily dissolved until saturation had occurred at 14° C., while maintaining the temperature at 14° C. with stirring. The reaction solution was held at 14° C. and was stirred for 36 hr. Subsequently, the powder precipitated in the reaction solution was collected and removed by Kiriyama type funnel. The filtrate was concentrated under reduced pressure to give 235 g of yellowish white powder. Purified water (500 g) was added to the yellowish white powder, and the mixture was heated to 60° C. for dissolution. The solution was slowly cooled to 5° C. in an ice bath for crystallization. The precipitated crystal was collected through Kiriyama type funnel. The collected crystal was placed in 200 mL of methanol, and the mixture was stirred for 10 min. After stirring, the crystal was collected through Kiriyama type funnel to give 5-mercapto-1-methylhydantoin as a white crystal (20 g (0.14 mol), yield 14% as calculated based on the starting compound 1-methylhydantoin).

Synthesis Example 3

<Synthesis of 5-methyl-5-mercaptomethylhydantoin>

A stirring blade, a thermometer, a pH electrode with a pH controller, and a starting compound feed pump were set in a 2000-mL four-necked flask. α-Chloroacetone (154 g (1.56 mol), content 94%; manufactured by Tokyo Chemical Industry Co., Ltd.) was added to this reactor, and this reactor was cooled in an ice bath so that the solution temperature was brought to 15° C. or below. A 20% aqueous sodium cyanide solution (514 g (102.9g as NaCN) (2.10 mol); manufactured by Junsei Chemical Corporation) was fed to this starting compound solution through a starting compound feed pump. In this case, a 18% aqueous hydrochloric acid solution was fed into the solution through a pump controlled with a pH controller so that pH is adjusted to 6 to 7. About one hr was necessary for the feed of the aqueous sodium cyanide solution, during which the reactor was cooled to maintain the temperature of the reaction solution at 16 to 18° C.

After the completion of the feed of the starting compound, the temperature was held at 16 to 18° C., and the mixture was stirred for about 30 min for ripening. The reaction solution as such was used in the next reaction.

A stirring blade, a thermometer, and the above starting compound feed pump as a reaction solution feed pump were set in a 5000-mL four-necked flask. Ammonium hydrogencarbonate (1032 g (13.1 mol); manufactured by Junsei Chemical Corporation) and 822 g of purified water were added to the reactor, and the mixture was stirred at 40° C. for 30 min. The above reaction solution (kept at 10° C. or below in an ice bath) was fed into the slurry of ammonium hydrogencarbonate through the pump over a period of about 4 hr. After the completion of the feed, the reaction solution was maintained at 40° C. and stirred for 2 hr. At the time when the reaction was completed, the reaction solution had a pH value of 7.15. After the completion of the reaction, the reaction solution was adjusted to pH 3 by the addition of 20% aqueous hydrochloric acid under ice cooling while maintaining the temperature at 20° C. or below. The pH-adjusted reaction solution was concentrated under reduced pressure until the volume of the reaction solution was approximately halved, resulting in the formation of a white crystal.

The white crystal thus obtained was collected through Kiriyama type funnel to give 5-chloromethyl-5-methyl hydantoin (127 g (0.78 mol, yield 50%)).

Purified water (138 g) and 246 g (3.1 mol) of 70% sodium hydrosulfide were added to and suspended in 50 g (0.31 mol) of 5-chloromethyl-5-methylhydantoin prepared above. The reactor was heated to 100° C. with stirring, and stirring was continued at 100° C. for additional 3 hr.

The reaction solution was cooled to 25° C. and was then adjusted to pH 3 by the addition of 95% sulfuric acid while blowing nitrogen gas through a glass tube with a glass filter from the bottom of the reactor. After the acidification, the reaction solution was concentrated until the volume of the reaction solution was reduced to 50% or less of the volume before the concentration. The resultant crystal was collected to give a crude crystal of 5-methyl-5-mercaptomethylhydantoin The crude crystal was dissolved in aqueous ammonia to prepare a 10% solution. This solution was set on the cathode side of an electrolytic cell, and 3% sulfuric acid was added to the anode side. A silver electrode was provided on the cathode side, a platinum electrode was provided on the anode side, and both the cells were partitioned with an ion exchange membrane (Selemion membrane, manufactured by Asahi Glass Co., Ltd.). A voltage of 15 V was applied across the electrodes while cooling in such a manner that the whole electrolytic cell was maintained at about 15° C. or below. As a result, the initial current value was 1.5 A. Energization was continued for about 15 hr. A catholyte was concentrated under reduced pressure to give 37 g of 5-methyl-5-mercaptomethylhydantoin powder (purity in powder 92%, yield 68%).

Example 1

<Preparation of First Liquid for Permanent Hair Waving>

Propylene glycol (10 g), 0.2 g of disodium edetate, and 1 g of polyoxyethylene stearyl ether were added to 80 g of purified water (water prepared by distillating water and passing the distilled water through an ion exchange filter), and the mixture was stirred for homogenization. 5-Mercaptohydantoin (2.9 g (22 mmol)) prepared in Synthesis Example 1 was added thereto by portions through a Pasteur pipette with stirring. After stirring for some time, this mixed solution was adjusted to desired pH value (pH 4.0, 6.0 and 7.0) by the addition of monoethanolamine. After thorough stirring, the pH value of the mixed solution was again adjusted. In this case, purified water was added so that the amount of the solution after the pH adjustment was 100 g, followed by stirring. Thus, the first liquid for permanent hair waving was obtained.

The results of the final pH measurement are shown within the parentheses in Table 1.

<Preparation of Second Liquid for Permanent Hair Waving>

Sodium bromate (5 g) was mixed with 95 g of purified water to prepare a second liquid for permanent hair waving.

<Permanent Waving Treatment>

Hair of a Chinese (length about 20 cm, 50 hairs) was wound in a wet state around a spiral curler (inner diameter: 13.5 mm), and the first liquid for permanent hair waving, which had been heated to 35° C. in an air conditioning room (temperature 35° C.), was evenly coated onto the hair through a pipette. Thereafter, the hair was lightly wiped to such an extent that the first liquid is not dropped from the hair. The hair after the treatment was allowed to stand at 35° C. for 20 min.

Next, the treated hair was wetted with the second liquid for permanent hair waving and was then allowed to stand at 35° C. for 10 min. After the completion of the treatment with the second liquid, the treated hair was removed from the curler. The treated hair was washed in water of 35° C., and the hair-bundle at its one end was fixed with a clip and was air dried in a hung state.

The waving efficiency was evaluated by a spiral rod method according to the procedure described in an extra edition of FRAGRANCE JOURNAL (No. 5, 1984, p. 421).

Specifically, the size of the hair after the permanent waving treatment was measured, and the waving efficiency was calculated by the following equation.

Waving efficiency (%)=(wave length of rod)/(average wave length L)×100 wherein average wave length $L=(l_1+l_2)/(n_1+n_2)$
where $l_1$ and $l_2$: distance between left and right wave crests excluding the first wave crest and the final wave crest in the spiral curler; and
$n_1$ and $n_2$: number of left and right wave crests in the spiral curler.

The results are shown in Table 1.

Example 2

The first liquid for permanent hair waving was prepared, and the waving efficiency was measured in the same manner as in Example 1, except that 3.2 g (22 mmol) of 5-mercapto-1-methylhydantoin prepared in Synthesis Example 2 was used instead of 5-mercaptohydantoin. The results are shown in Table 1.

Example 3

The first liquid for permanent hair waving was prepared, and the waving efficiency was measured in the same manner as in Example 1, except that 3.5 g (22 mmol) of 5-methyl-5-mercaptomethylhydantoin prepared in Synthesis Example 3 was used instead of 5-mercaptohydantoin. The results are shown in Table 1.

Comparative Example 1

The first liquid for permanent hair waving was prepared, and the waving efficiency was measured in the same manner as in Example 1, except that 2.66 g (22 mmol) of cysteine (manufactured by Junsei Chemical Corporation) was used instead of 5-mercaptohydantoin. The results are shown in Table 1.

TABLE 1

| | Waving efficiency, % (numerals within the parentheses are measure pH of first liquid) Target pH of first liquid | | |
|---|---|---|---|
| | pH 4.0 | pH 6.0 | pH 7.0 |
| Example 1 | 69 (pH 4.1) | 69 (pH 6.1) | 59 (pH 6.9) |
| Example 2 | 66 (pH 4.1) | 65 (pH 5.8) | 58 (pH 7.1) |
| Example 3 | 60 (pH 3.8) | 59 (pH 6.0) | 52 (pH 7.0) |
| Comparative Example 1 | 10 (pH 4.0) | 20 (pH 5.9) | 35 (pH 7.0) |

Test Example 1

The first agents for permanent hair waving (target pH values 4.0 and 7.0) prepared in Examples 1 to 3 and Comparative Example 1 were sensorily evaluated for odor by six women panelists on the order of 20 to 30 years old.

In the sensory evaluation, the odor of the cysteine-containing first agent prepared in Comparative Example 1 was used as a standard, and the number of panelists, who judged that the odor of the first agent was improved over that of the standard, was determined. The results were evaluated according to the following criteria.

0: All of the six panelists judged that the odor was not improved.

1: Among the six panelists, one or two panelists judged that the odor was improved.

2: Among the six panelists, three or four panelists judged that the odor was improved.

3: Among the six panelists, five or six panelists judged that the odor was improved.

The results are shown in Table 2.

TABLE 2

| | Results of sensory evaluation Target pH of first liquid | |
|---|---|---|
| | pH 4.0 | pH 7.0 |
| First liquid of Example 1 | 2 | 3 |
| First liquid of Example 2 | 3 | 3 |

TABLE 2-continued

| | Results of sensory evaluation Target pH of first liquid | |
|---|---|---|
| | pH 4.0 | pH 7.0 |
| First liquid of Example 3 | 3 | 3 |

Table 2 shows that, as compared with the commonly adopted cysteine permanent wave, even in the neutral to acidic pH range, the agent for permanent hair waving containing the heterocyclic mercapto compound according to the present invention has a more stable waving efficiency and, at the same time, has a significant improvement in odor.

The invention claimed is:

1. An agent for permanent hair waving comprising at least one heterocyclic mercapto compound represented by formula (1) in a content of 0.2 to 15% by mass:

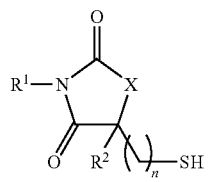

(1)

wherein $R^1$ and $R^2$ each independently represent a hydrogen atom or an optionally substituted alkyl group having 1 to 5 carbon atoms; X represents —O—, —S—, —NH—, or —NR$^3$—; $R^3$ represents an alkyl group having 1 to 5 carbon atoms; n is an integer of 0 to 2; and, when n is 2, group SH may be attached to any carbon atom of an alkylene group having 2 carbon atoms.

2. The agent for permanent hair waving according to claim 1, wherein $R^1$ and $R^2$ in formula (1) each independently represent a hydrogen atom, an alkyl group having 1 to 5 carbon atoms, or a substituted alkyl group having 2 to 5 carbon atoms in which two or more methylene groups are bonded through an ether bond, a thioether bond, or an amine bond.

3. The agent for permanent hair waving according to claim 1, wherein $R^1$ and $R^2$ in formula (1) each independently represent a hydrogen atom or an alkyl group having 1 to 4 carbon atoms.

4. The agent for permanent hair waving according to claim 1, wherein X in formula (1) represents —NH— or —NR$^3$—.

5. The agent for permanent hair waving according to claim 1, wherein X in formula (1) represents —NH—, and $R^1$ and $R^2$ each independently represent a hydrogen atom or a methyl group.

6. The agent for permanent hair waving according to claim 1, wherein X in formula (1) represents —NR$^3$—, and $R^1$ and $R^2$ each independently represent a hydrogen atom or a methyl group.

7. The agent for permanent hair waving according to claim 1, wherein the pH value is 2.5 to 8.5.

8. The agent for permanent hair waving according to claim 1, wherein a perfume is further contained.

9. A method for permanent hair waving comprising applying to the hair a an agent permanent hair waving according to claim 1.

* * * * *

UNITED STATES PATENT AND TRADEMARK OFFICE
CERTIFICATE OF CORRECTION

| | |
|---|---|
| PATENT NO. | : 8,066,977 B2 |
| APPLICATION NO. | : 11/884413 |
| DATED | : November 29, 2011 |
| INVENTOR(S) | : Akira Shibuya, Shinichi Yorozuya and Makoto Saito |

Page 1 of 1

It is certified that error appears in the above-identified patent and that said Letters Patent is hereby corrected as shown below:

In the Claims

Column 18, lines 29-31, cancel the text of claim 9 in the patent, and insert the following claim:

-- 9. A method for permanent hair waving comprising applying to the hair an agent for permanent hair waving according to claim 1. --

Signed and Sealed this
Tenth Day of June, 2014

Michelle K. Lee
*Deputy Director of the United States Patent and Trademark Office*